United States Patent [19]
Fujita

[11] Patent Number: 5,847,103
[45] Date of Patent: Dec. 8, 1998

[54] EXPRESSION INHIBITOR COMPRISING AN ANTISENSE OLIGONUCLEOTIDE DERIVATIVE CORRESPONDING TO HUMAN INTERLEUKIN-6 RECEPTOR

[75] Inventor: Jun Fujita, Kyoto, Japan

[73] Assignee: Chugai Seiyaku Kabushiki Kaisha, Tokyo, Japan

[21] Appl. No.: 549,005

[22] Filed: Oct. 27, 1995

[30] Foreign Application Priority Data

Apr. 30, 1992 [JP] Japan .................................. 5-104561

[51] Int. Cl.⁶ .......................... C12N 15/00; C12N 15/09; C12N 15/11
[52] U.S. Cl. .......................... 536/24.1; 435/375; 435/455; 536/23.1
[58] Field of Search .............................. 514/44; 536/23.1, 536/23.5, 24.1, 24.5; 435/240.2, 455, 375; 530/351

[56] References Cited

U.S. PATENT DOCUMENTS 5,135,917  8/1992  Burch ........................................ 514/44

FOREIGN PATENT DOCUMENTS 2288898  11/1990  Japan .

OTHER PUBLICATIONS

Heidenreich et al (1995). Molecular Medicine Today 1, 128–133.
Gura, (1995) "Antisense Has Growing Pains". Science 270, 575–577.
Wagner (1994). Nature 372, 333–335.
DeMesmaeker (1995), Acc. Chem. Res. 28 (9), 366–374.
Yamasaki et al. (1988). Science 241, 825–828.
Fujita et al. (1992) ACTA Urologica Saponica 38 (11), 1333–1336.
Uhlmann et al (1990). Chemical Reviews 90 (4), 543–583.
Monia et al (1992) The Journal of Biological Chemistry 267 (28), 19954–19962.
Genomics, vol. 10 (No. 3), pp. 539–546 (1991), J. Szpirer et al., "The Interleukin–6–Dependent DNA Binding Protein Gene".
Chemistry; vol. 46, No. 10, pp. 681 to 684 (Kagaku Dojin (Kyoto)) Oct. 1989 (10. 1989), Akira Murakami, "Antisense DNA method".

*Primary Examiner*—Brian R. Stanton
*Attorney, Agent, or Firm*—Lyon & Lyon LLP

[57] ABSTRACT

There is provided an inhibitor of expression of human IL-6R, whose effective component is an antisense oligonucleotide derivative which hybridizes to the region of a nucleotide sequence of 9 to 30 nucleotides including the translation initiation codon of mRNA coding for human interleukin-6 receptor (IL-6R).

8 Claims, 1 Drawing Sheet

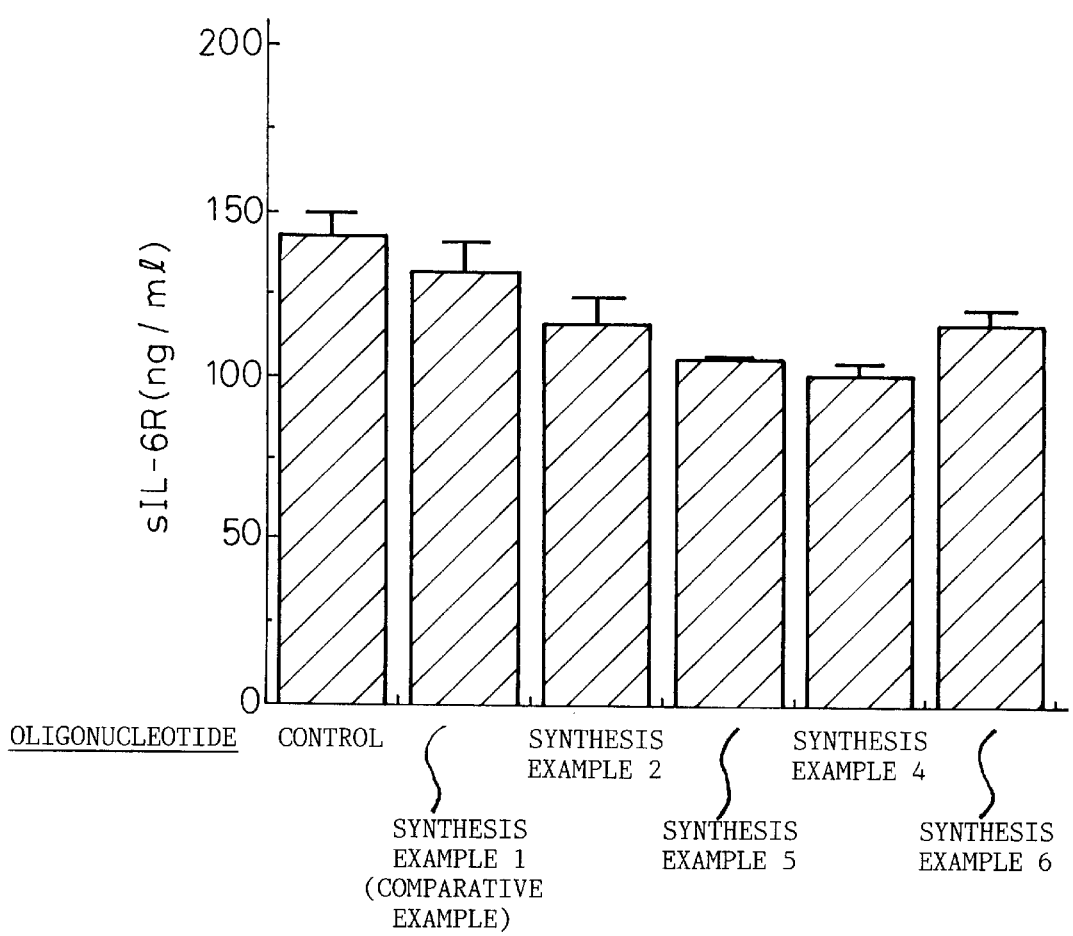

EXPRESSION INHIBITOR COMPRISING AN ANTISENSE OLIGONUCLEOTIDE DERIVATIVE CORRESPONDING TO HUMAN INTERLEUKIN-6 RECEPTOR

This application is a continuation-in-part of PCT/JP93/01736 filed on Nov. 29, 1993, entitled "EXPRESSION INHIBITOR COMPRISING AN ANTISENSE OLIGONUCLEOTIDE DERIVATIVE CORRESPONDING TO HUMAN INTERLEUKIN-6 RECEPTOR", claiming priority from 5-104561, filed in Japan on Apr. 30, 1993.

TECHNICAL FIELD

The present invention relates to an antisense oligonucleotide derivative which is useful as a drug to inhibit the expression of human interleukin-6 receptor (human IL-6R).

BACKGROUND ART

Human interleukin-6 (human IL-6) is a cytokine which has been cloned as a factor which induces final-stage differentiation of B cells to antibody-producing cells (Kishimoto T. et al., Blood 74, 1–10, 1989), and it is presently known to have a variety of actions including the induction of acute phase protein in the liver (Kishimoto T. et al., Blood 74, 1–10, 1989).

In addition, it has been reported that human IL-6 is produced not only by lymphocytes, but also by fibroblasts, vascular endothelial cells, the bladder cancer cell line T24 and glioblastomas (Kohase M. et al., J. Cell Physiol. 132, 271–278, 1978; Meir EV et al., Cancer Res. 50, 6683–6688, 1990), and also that its target cells range among a variety of different types (Kishimoto T. et al., Blood 74, 1–10, 1989).

Recently years, Kawano M. et al. have reported that human IL-6 functions as an autocrine growth factor in myeloma cells (Kawano M. et al., Nature, 332, 83–85, 1988), and the same has also been reported in renal cell carcinoma (Miki S. et al., FEBS Lett. 250, 607–610, 1989).

The signal from human IL-6 for cells to proliferate or differentiate is known to be transmitted to cells via human IL-6R and glycoprotein gp130which are present on cell surfaces (Taga T., et al. Cell 58, 573–581, 1989; Hibi M. et al., Cell 68, 1149–1157, 1990).

As a method for suppressing the function of genes which are the cause of diseases, in recent years the use of oligonucleotide (antisense oligonucleotides) which are complementary to mRNAs transcribed from DNA, to suppress the expression of a corresponding proteins has been proposed (Murakami, Kagaku, 46, 681–684, 1991).

In addition, modification of antisense oligonucleotides, such as methyl phosphonate-type derivatives wherein an oxygen atom of the phosphate group of a nucleotide is replaced with a methyl group and phosphorothioate-type derivatives wherein it is replaced with a sulfur atom, are known to have improved lifetime, stability and efficiency of incorporation into cells (Murakami, ibid), and these antisense nucleotides have been shown actually to inhibit viral protein synthesis (Agris, C. H. et al., Biochemistry, 25, 6268–6275, 1986).

On the basis of such an idea, Levy, et al. have confirmed that the inhibition of translation of IL-6 mRNA by antisense oligonucleotides suppresses the proliferation of myeloma cell lines for which human IL-6 is a proliferating factor. (Levy Y. et al., J. Clin. Invest., 88, 696–699, 1991).

Nevertheless, antisense oligonucleotide derivatives which significantly suppress the expression of IL-6R in the various cells which express human IL-6R are not known.

DISCLOSURE OF THE INVENTION

It is, therefore, an object of the present invention to provide an antisense oligonucleotide derivative which inhibits the expression of human IL-6R.

More specifically, the present invention provides an inhibitor of expression of human IL-6R which comprises an antisense oligonucleotide derivative corresponding to a continuous base sequence of at least 9 bases including the translation initiation codon of mRNA coding for human IL-6R.

BRIEF DESCRIPTION OF THE DRAWINGS

FIG. 1 is a histogram showing suppression by the antisense oligonucleotide derivative of the present invention of the expression of soluble IL-6R in an experiment.

DEFINITIVE MODE FOR CARRYING OUT THE INVENTION

The present inventors have synthesized antisense oligonucleotide derivatives corresponding to a continuous nucleotide sequence of at least 9 nucleotides including the translation initiation codon of mRNA coding for human IL-6R, and have discovered that they suppress the proliferation of human renal cell carcinoma in cell cultures thereof.

A preferred embodiment of the present invention uses an antisense oligonucleotide derivative corresponding to a continuous base sequence consisting of 9 to 30, and preferably 12 to 25, nucleotides including the translation initiation codon of mRNA coding for human IL-6R.

The term "antisense oligonucleotide" as used here does not necessarily mean that all of the nucleotides corresponding to the nucleotides comprising a given domain of DNA or mRNA must be complementary, and there may be some mismatching so long as the oligonucleotide may be stably hybridized to the DNA or mRNA.

The sequence of the human IL-6R translation initiation codon and its vicinity is as follows (see, for example, Japanese Unexamined Patent Publication No. 2-288898) (SEQ ID NO: 1).

```
                                                            -1
5' CTGTCCGCCTCTGCGGGACCATGGAGTGGTAGCCGAGGAGGAAGC

1
ATG CTG GCC GTC GGC TGC GCG CTG CTG GCT GCC CTG CTG GCC
Met Leu Ala Val Gly Cys Ala Leu Leu Ala Ala Leu Leu Ala
GCG 3'
Ala
```

The nucleotide sequences of the antisense oligonucleotide derivatives of the present invention thus include the codon ATG for the first amino acid Met, and may be appropriately selected from the continuous nucleotide sequence above from the 5' end to the 3' end.

According to one embodiment of the present invention, the expression-inhibiting oligonucleotide is an antisense oligonucleotide corresponding to a nucleotide sequence comprising the initiation codon ATG of Sequence No. 1 and a sequence downstream therefrom, and it has, for example, the nucleotide sequence which is complementary to the nucleotide sequence of the codons encoding from the Met at the first position to the Gly at the 5th position, i.e., 5' GCCGACGGCCAGCAT-3' (SEQ ID NO: 2).

According to a preferred embodiment of the present invention, the expression-inhibiting oligonucleotide is an antisense oligonucleotide corresponding to a nucleotide sequence comprising the initiation codon of SEQ ID NO: 1 and a sequence upstream therefrom. An example of such an oligonucleotide is one which has a nucleotide sequence which is complementary to the initiation codon ATG and 17 nucleotides upstream therefrom, i.e., 5'-CATGCTTCCTCCTCGGCTAC-3' (SEQ ID NO: 3). Another example thereof is the nucleotide sequence which is complementary to the initiation codon and 12 nucleotides upstream therefrom, i.e., 5'-CATGCTTCCTCCTCG-3' (SEQ ID NO: 4).

According to another preferred embodiment of the present invention, the expression-inhibiting oligonucleotide is an antisense oligonucleotide corresponding to a nucleotide sequence comprising the initiation codon of Sequence No. 1 and sequences upstream and downstream therefrom. An example of such an oligonucleotide is one which has a nucleotide sequence which is complementary to the nucleotide sequence comprising the initiation codon ATG, 11 nucleotides upstream therefrom and 6 nucleotides downstream therefrom, i.e., 5'-GGCCAGCATGCTTCCTCCTC-3' (SEQ ID NO: 5).

When the oligonucleotide derivatives used according to the present invention are deoxyribonucleotides, their respective structures are as shown by structural formula 1, wherein X may independently be a sulfur atom (S), a lower alkyl group or a primary or secondary amine. Y may independently be an oxygen atom (O) or a sulfur atom (S). B may be selected from adenine, guanine, thymine or cytosine, and each one is selected so as to define an oligonucleotide essentially complementary to the DNA or mRNA coding for the human IL-6 receptor. R is independently a hydrogen atom or a dimethoxytrityl or lower alkyl group, and n is 7 to 28.

As examples of preferred oligonucleotide derivatives there may be mentioned lower alkyl phosphonate-modified ones such as the methyl phosphonate-types mentioned above and ethyl phosphonate-types, as well as phosphorothioate-modified and phosphoroamidate-modified ones (see structural formula 2 below).

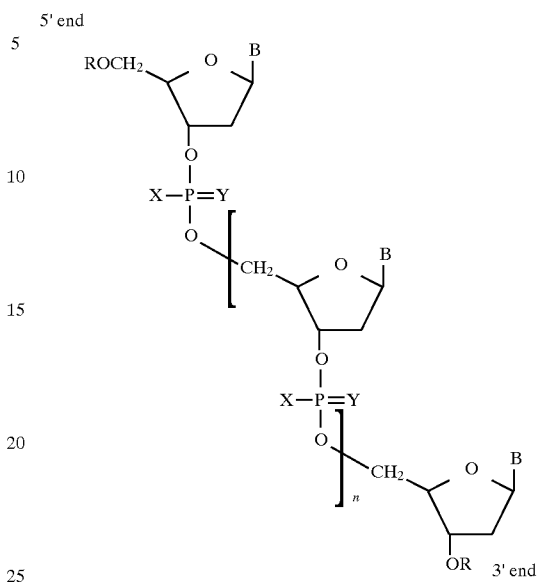

Structural formula 1

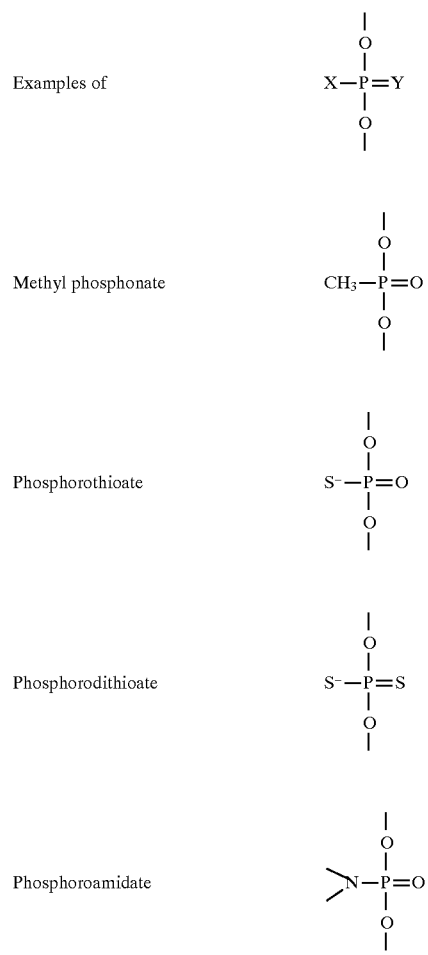

Structural formula 2

-continued

Trialkyl phosphate 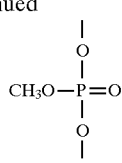

Oligonucleotides wherein X and Y of the structural formula are oxygen are easily synthesized using a commercially available DNA synthesizer (for example, one produced by Applied Biosystems Co.).

The method of synthesis used may be solid phase synthesis using phosphoroamidite, solid phase synthesis using hydrogen phosphonate, etc.

See, for example, T. Atkinson, M. Smith, in Oligonucleotide Synthesis: A Practical Approach, ed. M. J. Gait, IRL Press, 35–81 (1984); M. H. Caruthers, Science, 230, 281 (1985); A. Kume, M. Fujii, M. Sekine, M. Hata, J. Org. Chem., 49, 2139(1984); B. C. Froehler, M. Matteucci, Tetrahedron Lett., 27, 469(1986); P. J. Garegg, I. Lindh, T. Regberg, J. Stawinski, R. Stromberg, C. Henrichson, ibid., 27, 4051(1986); B. S. Sproat, M. J. Gait, in Oligonucleotide Synthesis: A Practical Approach, ed. M. J. Gait. IRL Press, 83–115(1984); S. L. Beaucage and M. H. Caruthers, Tetrahedron Lett., 22, 1859–1862(1981); M. D. Matteucci and M. H. Caruthers, Tetrahedron Lett., 21, 719–722(1980); M. D. Matteucci and M. H. Caruthers, J. Am. Chem. Soc., 103, 3185–3191(1981).

Triester phosphate-modified oligonucleotides wherein X is a lower alkoxy group may be obtained by a conventional method, such as treating an oligonucleotide obtained by chemical synthesis with a DMF/methanol/2,6-lutidine solution containing tosyl chloride (Moody H. M., et al., Nucleic Acids Res., 17, 4769–4782(1989)).

Alkyl phosphonate-modified oligonucleotides wherein X is an alkyl group may be obtained by a conventional method using, for example, a phosphoamidite (M. A. Dorman, et al., Tetrahedron, 40, 95–102(1984); K. L. Agarwal and F. Riftina, Nucleic Acids Res., 6, 3009–3024(1979)).

Phosphorothioate-modified oligonucleotides wherein X is a sulfur atom may be obtained by a conventional method, such as solid phase synthesis using sulfur (C. A. Stein, et al., Nucleic Acids Res., 16, 3209–3221(1988) or solid phase synthesis using tetraethylthiuram disulfide (H. Vu and B. L. Hirschbein, Tetrahedron Lett., 32, 3005–3008(1991)).

Phosphorodithioate-modified oligonucleotides wherein X and Y are both sulfur atoms may be obtained, for example, by solid phase synthesis whereby bis-amidite is converted to thioamidite and subjected to the action of sulfur (W. K. -D. Brill, et al., J. Am. Chem. Soc., 111, 2321–2322(1989)).

Phosphoroamidate-modified oligonucleotides wherein X is a primary or secondary amine may be obtained by solid phase synthesis by, for example, treatment of a hydrogen phosphonate with a primary or secondary amine (B. Froehler, et al. Nucleic Acids Res., 16, 4831–4839(1988)). Alternatively, they may be obtained by oxidation of an amidite with tert-butylhydroperoxide (H. Ozaki, et al., Tetrahedron Lett., 30, 5899–5902(1989)).

Purification and confirmation of purity may be accomplished by high performance liquid chromatography or polyacrylamide gel electrophoresis. Confirmation of the molecular weight may be made by Electrospray Ionization Mass Spectrometry or Fast Atom Bombardment-Mass Spectrometry.

The antisense oligonucleotide derivatives of the present invention may be synthesized or derived in any manner so long as they have a sequence which hybridizes to the nucleotide sequence of DNA or mRNA coding for human IL-6R.

The antisense oligonucleotide derivatives of the present invention act on human IL-6R-producing cells, binding to the DNA or mRNA coding for human IL-6R to inhibit its transcription or translation respectively, and thereby suppress the expression of human IL-6R to result in suppression of the effects of human IL-6. The effects of human IL-6 which are suppressed by the antisense oligonucleotide derivatives of the present invention include the effects of thrombocytosis, increased antibody-production, induction of acute phase protein, tumor cell growth, and neuronal differentiation, etc.

Thus, it is believed that the antisense oligonucleotide derivatives of the present invention are effective for the therapy of diseases resulting from these effects, including cancers such as renal carcinoma, myeloma, Lennert T lymphoma, and Kaposi's sarcoma; autoimmune diseases such as chronic rheumatoid arthritis; mesangial proliferative nephritis, psoriasis, cancerous cachexia, endotoxie shock accompanying infection, and the like.

The antisense oligonucleotide derivatives of the present invention may be used in the form of an external preparation, such as an application or poultice, in admixture with an appropriate base which is inert thereto. If necessary, an excipient, isotonic agent, solubilizer, stabilizer, antiseptic, soothing agent or the like may be added, to make tablets, powder, granules, capsules, liposome capsules, injections, liquid, nasal drops, etc., or a lyophilized agent may be used. These may be prepared according to conventional methods.

The antisense oligonucleotide derivatives of the present invention are either applied directly to the affected area of the patient, or they are applied to the patient by intravascular administration to effectively reach the affected site. There may also be used an antisense encapsulating material to prolong the duration of action and enhance the membrane permeability. Examples include liposomes, poly-L-lysine, lipids, and cholesterol lipofectin and derivatives thereof.

An appropriate dosage of the antisense oligonucleotide derivatives of the present invention may be used based on proper adjustment reflecting the conditions of the patient. For example, administered doses may be in the range of 0.1 to 100 mg/kg, and preferably 0.1 to 50 mg/kg.

The present invention will now be explained in more detail with reference to the following examples.

EXAMPLES

Synthesis Example 1

Synthesis of 5'-GCCGACGGCCAGCAT-3' (SEQ ID NO: 2)

A 15 nucleotide sequence (GCCGACGGCCAGCAT) (SEQ ID NO: 2) complementary to 5 codons starting with the initiation codon of human IL-6 receptor mRNA was synthesized with a DNA synthesizer (Gene Assembler Plus, product of Pharmacia Co.) for use as a human IL-6R antisense oligonucleotide.

Synthesis Example 2

Synthesis of 5'-GCCGACGGCCAGCAT-3' (SEQ ID NO: 2) (phosphorothioate-modified)

The dimethoxytrityl group of 5'-dimethoxytritylthymidine (1 μmol), of which the 3'-hydroxyl group has been bonded to a carrier, is deprotected with trichloroacetic acid and condensed at its 5'-hydroxyl group with a 5'-dimethoxytrityldeoxyadenosine β-cyanoethylphosphoamidite derivative using tetrazole, and after the phosphorus is sulfated with tetraethylthiuram disulfide, the unreacted 5'-hydroxyl groups are acetylated with acetic anhydride and 4-dimethylaminopyridine.

This procedure of deprotection, condensation, sulfation and acetylation is repeated. The final 5'-dimethyoxytrityl deoxyguanosine β-cyanoethylphosphoamidite derivative is condensed and sulfated to obtain a 15-mer phosphorothioate-modified oligonucleotide (the procedure described above was carried out using a DNA synthesizer, model 381A of Applied Biosystems) which is then separated from the carrier with 2 ml of concentrated ammonia water, after which the cyanoethyl groups are removed from the phosphorus and the protecting groups attached to the adenine, guanine and cytosine residues are also removed.

While the resultant 5'-dimethoxytrityloligonucleotide phosphorothioate is as yet unpurified, or after its purification by high performance liquid chromatography, the 5'-dimethoxy protecting groups are removed with 5 ml of trifluoroacetic acid. If necessary, the resultant oligonucleotide phosphorothioate is then purified by high performance liquid chromatography, to obtain about 2.09 mg of the desired 5'-GCCGACGGCCAGCAT-3' (SEQ ID NO: 2) (phosphorothioate-modified oligonucleotide).

Synthesis Example 3
Synthesis of 5'-GCGCAGCCGACGGCCAGCAT-3' (SEQ ID NO: 6) (phosphorothioate-modified)

The same procedure is followed as in Synthesis Example 2, to obtain about 1.81 mg of the desired 5'-GCGCAGCCGACGGCCAGCAT-3' (SEQ ID NO: 6) (phosphorothioate-modified).

Synthesis Example 4
Synthesis of 5'-CATGCTTCCTCCTCGGCTAC-3' (SEQ ID NO: 3) (phosphorothioate-modified)

The same procedure is followed as in Synthesis Example 2, to obtain about 1.96 mg of the desired 5'-CATGCTTCCTCCTCGGCTAC-3' (SEQ ID NO: 3) (phosphorothioate-modified).

Synthesis Example 5
Synthesis of 5'-CATGCTTCCTCCTCG-3' (SEQ ID NO: 4) (phosphorothioate-modified)

The same procedure is followed as in Synthesis Example 2, to obtain about 1.91 mg of the desired 5'-CATGCTTCCTCCTCG-3' (SEQ ID NO: 4) (phosphorothioate-modified).

Synthesis Example 6
Synthesis of 5'-GGCCAGCATGCTTCCTCCTC-3' (SEQ ID NO: 5) (phosphorothioate-modified)

The same procedure is followed as in Synthesis Example 2, to obtain about 1.08 mg of the desired 5'-GGCCAGCATGCTTCCTCCTC-3' (SEQ ID NO: 5) (phosphorothioate-modified).

Example 1: Suppressing effect on expression of human soluble IL-6R

An NcoI fragment was prepared from the human IL-6R gene (see FIGS. 2 and 3 of Japanese Unexamined Patent Publication No. 2-288898), a TAG linker (CATGTAGAGATCT) was added thereto, and the fragment was inserted into the CHO expression vector pdR (Lit.: Hasegawa M., Eur. J. Biochem., 210, 9–12 (1992)) to construct a soluble IL-6R expression vector (pRNDR1).

This plasmid pRNDR1 was introduced into dhfr CHO cells by the calcium phosphate method and amplified in the presence of MTX. Finally, 1 μM MTX-resistant, soluble IL-6R-producing CHO cells (CHO•RN1) were obtained. The pRNDR1 plasmid includes a soluble IL-6R gene beginning at the 26th nucleotide upstream (5') of the translation initiation codon ATG of Sequence No. 1.

Culturing of the cells was performed in IMDM medium (product of GIBCO Co.) containing 1% FCS (product of Boehringer-Mannheim Co.) and 1 μM MTX.

A 75 μl portion of 10 μM human IL-6R antisense oligonucleotide was added to 75 μl of CHO•RN1 culture solution ($6.6 \times 10^4$ cells/ml) on a 96-well culture plate, and the culturing was conducted in an incubator at 37° C., in an atmosphere of 5% $CO_2$.

After 24 hours of culturing, the amount of soluble IL-6R in the culture supernatant was determined by the sandwich ELISA method using mouse anti-IL-6R monoclonal antibody (MT-18) (see Japanese Unexamined Patent Publication No. 2-288898) and rabbit anti-IL-6R polyclonal antibody.

As a control, the measurement was made using only the culture supernatant, and for comparison the measurement was made using the oligonucleotide obtained in Synthesis Example 1.

The antisense oligonucleotide derivative corresponding to human IL-6R exhibited an expression-suppressing effect on soluble IL-6R (FIG. 1).

INDUSTRIAL APPLICABILITY

The human IL-6R expression inhibitor of the present invention promises to be useful as a drug to suppress the effects of human interleukin-6.

What we claim is:

1. An inhibitor of expression of human IL-6 receptor, consisting of an antisense oligonucleotide wherein said antisense oligonucleotide has the nucleotide sequence GCCGACGGCCAGCAT (SEQ ID NO. 2).

2. An inhibitor of expression of human IL-6 receptor, consisting of an antisense oligonucleotide wherein said antisense oligonucleotide has the nucleotide sequence CATGCTTCCTCCTCGGCTAC (SEQ ID NO. 3).

3. An inhibitor of expression of human IL-6 receptor, consisting of an antisense oligonucleotide wherein said antisense oligonucleotide has the nucleotide sequence GATGCTTCCTCCTCG (SEQ ID NO. 4).

4. An inhibitor of expression of human IL-6 receptor, consisting of an antisense oligonucleotide wherein said antisense oligonucleotide has the nucleotide sequence GGCCAGCATGCTTCCTCCTC (SEQ ID NO. 5).

5. An inhibitor of expression of human IL-6 receptor, consisting an antisense oligonucleotide derivative, wherein said antisense oligonucleotide derivative has the structure:

Stuctural formula 1

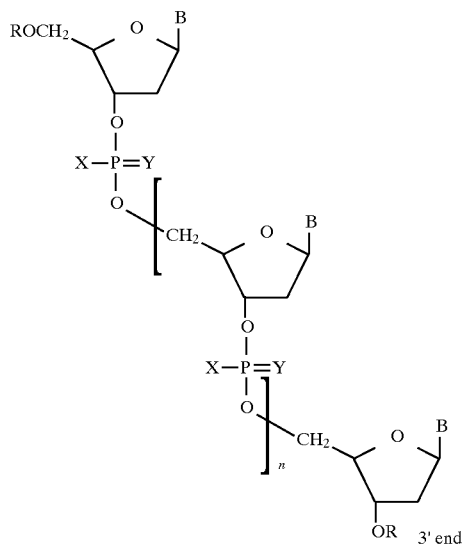

wherein X is independently sulfur, a lower alkyl group, a primary amine, a secondary amine, or a lower alkoxy;

Y is independently oxygen or sulfur;

B is adenine, guanine, thymine or cytosine;

R is independently hydrogen, dimethoxytrityl or a lower alkyl group; and n is 13, and said antisense oligonucleotide derivative has the nucleotide sequence GCCGACGGCCAGCAT (SEQ ID NO. 2).

6. An inhibitor of expression of human IL,6 receptor, consisting of an antisense oligonucleotide derivative, wherein said antisense oligonucleotide derivative has the structure:

Structural formula 1

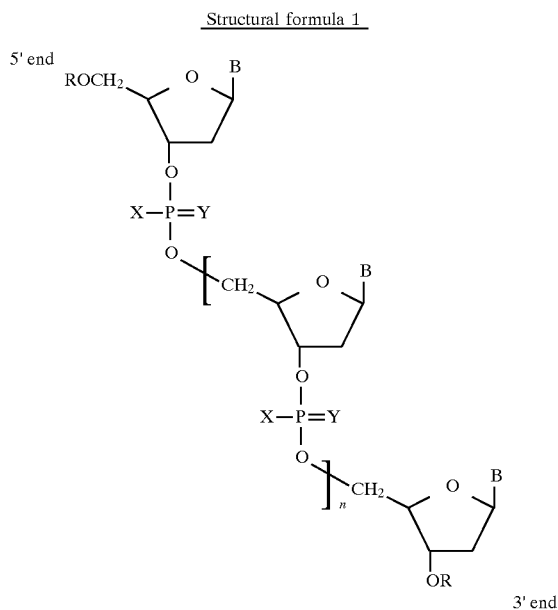

wherein X is independently sulfur, a lower alkyl group, a primary amine, a secondary amine, or a lower alkoxy;

Y is independently oxygen or sulfur;

B is adenine, guanine, thymine or cytosine;

R is independently hydrogen, dimethoxytrityl or a lower alkyl group; and n is from 18, and said antisense oligonucleotide derivative has the nucleotide sequence CATGCTTCCTCCTCGGCTAC (SEQ ID NO. 3).

7. An inhibitor of expression of human IL-6 receptor, consisting of an antisense oligonucleotide derivative, wherein said antisense oligonucleotide derivative has the structure:

Structural formula 1

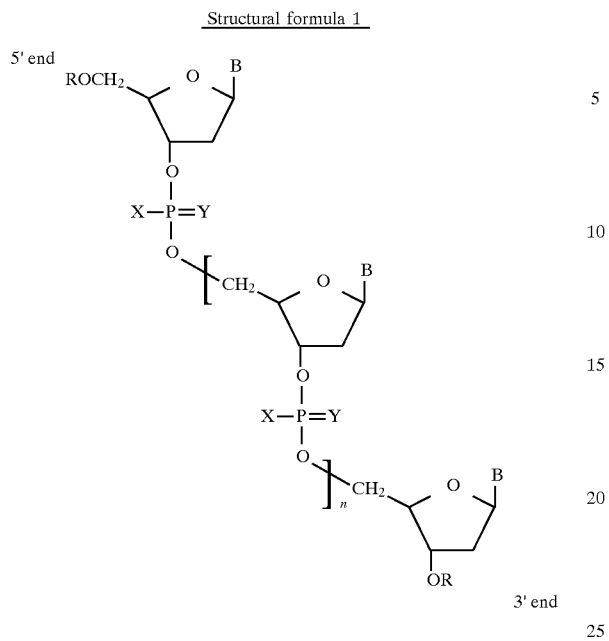

wherein X is independently sulfur, a lower alkyl group, a primary amine, a secondary amine, or a lower alkoxy;

Y is independently oxygen or sulfur;

B is adenine, guanine, thymine or cytosine;

R is independently hydrogen, dimethoxytrityl or a lower alkyl group; and n is from 13, and said antisense oligonucleotide derivative has the nucleotide sequence GATGCTTCCTCCTCG (SEQ ID NO. 4).

8. An inhibitor of expression of human IL-6 receptor, consisting of an antisense oligonucleotide derivative, wherein said antisense oligonucleotide derivative has the structure:

Structural formula 1

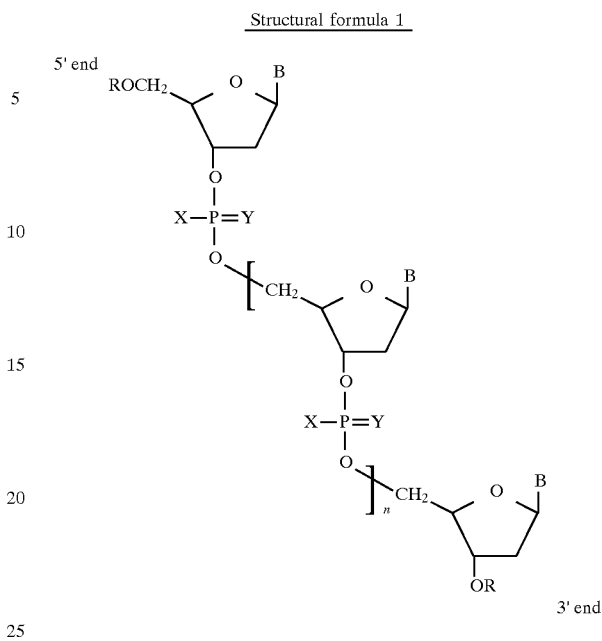

wherein X is independently sulfur, a lower alkyl group, a primary amine, a secondary amine, or a lower alkoxy;

Y is independently oxygen or sulfur;

B is adenine, guanine, thymine or cytosine;

R is independently hydrogen, dimethoxytrityl or a lower alkyl group; and n is from 18, and said antisense oligonucleotide derivative has the nucleotide sequence GGCCAGCATGCTTC-CTCCTC (SEQ ID NO. 5).

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
  ( A ) LENGTH: 90 base pairs
  ( B ) TYPE: nucleic acid ( C ) STRANDEDNESS: single
            ( D ) TOPOLOGY: linear ( x i ) SEQUENCE DESCRIPTION: SEQ ID NO: 1:

CTGTCCGCCT  CTGCGGGACC  ATGGAGTGGT  AGCCGAGGAG  GAAGC ATG CTG           51
                                                      Met Leu
                                                       1

GCC GTC GGC TGC GCG CTG CTG GCT GCC CTG CTG GCC GCG                     90
Ala Val Gly Cys Ala Leu Leu Ala Ala Leu Leu Ala Ala
     5                   10                  15

( 2 ) INFORMATION FOR SEQ ID NO: 2:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: synthetic DNA ( x i ) SEQUENCE DESCRIPTION: SEQ ID NO: 2:

GCCGACGGCC AGCAT                                                        15

( 2 ) INFORMATION FOR SEQ ID NO: 3:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: synthetic DNA ( x i ) SEQUENCE DESCRIPTION: SEQ ID NO: 3:

CATGCTTCCT CCTCGGCTAC                                                   20

( 2 ) INFORMATION FOR SEQ ID NO: 4:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( i i ) MOLECULE TYPE: synthetic DNA ( x i ) SEQUENCE DESCRIPTION: SEQ ID NO: 4:

CATGCTTCCT CCTCG                                                        15

( 2 ) INFORMATION FOR SEQ ID NO: 5:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: synthetic DNA ( x i ) SEQUENCE DESCRIPTION: SEQ ID NO: 5:

GGCCAGCATG CTTCCTCCTC                                                   20

( 2 ) INFORMATION FOR SEQ ID NO: 6:

( i ) SEQUENCE CHARACTERISTICS:
                ( A ) LENGTH: 20 base pairs
                ( B ) TYPE: nucleic acid
                ( C ) STRANDEDNESS: single (D) TOPOLOGY: linear (ii) MOLECULE TYPE: synthetic DNA (xi) SEQUENCE DESCRIPTION: SEQ ID NO: 6:

GCGCAGCCGA CGGCCAGCAT    20